United States Patent [19]

Rozas

[11] Patent Number: 4,978,351
[45] Date of Patent: Dec. 18, 1990

[54] GUIDING INSTRUMENT TO PIERCE THE BONE CORTICAL, AUXILIARY IN THE LOCATION OF THE HOLES FOR INTRA-MARROW PINS

[76] Inventor: Fernando C. Rozas, 112 Colina Rumorosa Street, Bulevares, Naucalpan, Mexico

[21] Appl. No.: 340,232

[22] Filed: Apr. 19, 1989

[30] Foreign Application Priority Data

Sep. 28, 1988 [MX] Mexico .................................. 13200

[51] Int. Cl.$^5$ ............................................ A61B 17/56
[52] U.S. Cl. ...................................... 606/98; 606/96; 606/102
[58] Field of Search ............ 128/92 Y, 92 YZ, 92 YY, 128/92 YF, 92 YE, 92 V, 92 VD, 92 VL, 92 VZ, 92 R; 606/96, 98, 102

[56] References Cited

U.S. PATENT DOCUMENTS

| | | | |
|---|---|---|---|
| 2,200,120 | 5/1940 | Nauth | 128/92 VD |
| 2,531,734 | 11/1950 | Hopkins | 128/92 VD |
| 3,835,849 | 9/1974 | McGuire | 128/92 VD |
| 3,867,932 | 2/1975 | Huene | 128/92 V |
| 4,235,428 | 11/1980 | Davis | 128/92 YE X |
| 4,364,381 | 12/1982 | Sher et al. | 128/92 VD X |
| 4,622,959 | 11/1986 | Marcus | 606/98 X |
| 4,917,111 | 4/1990 | Pennig et al. | 606/97 |

FOREIGN PATENT DOCUMENTS

| | | | |
|---|---|---|---|
| 168885 | 3/1951 | Austria | 128/92 VD |
| 3412362 | 10/1985 | Fed. Rep. of Germany | 128/92 VD |
| 839510 | 6/1981 | U.S.S.R. | 128/92 VD |
| 908346 | 2/1982 | U.S.S.R. | 128/92 VD |

OTHER PUBLICATIONS

Zimmer Manf., 2/1947, p. 32, Key Dual Bone Plate Outfit.

Primary Examiner—Robert A. Hafer
Assistant Examiner—Kevin G. Rooney
Attorney, Agent, or Firm—McAulay Fisher Nissen & Goldberg

[57] ABSTRACT

An instrument for positioning of intra-marrow pin orifices and to guide a bit for a drilling of a bone cortical, in which an elongated member having a width and thickness suitable to resist a surgeon's pushing and a grip at one end thereof and a substantially narrowed portion at the other end for reducing as much as possible the size of an incision to be made thereby in a patient's tissues, and having a projection positioned between the ends closer to the other end and orthogonal thereto is provided with a gauge thereon, and a slidable alignment body having slidably connected with the projection for slidably connecting the prismatic body with the projection, and the slidable alignment body is fixedly coupled by a screw with the elongated member at a position thereon closer to the other end and locking the slidable alignment body to the elongated member at selected positions on the projection and the alignment body is slidably movable to different previously selected positions on the projection; and the alignment body has two spaced orifices oriented transversely to the projection for receiving and guiding a bit into alignment with an orifice in the intra-marrow pin.

19 Claims, 3 Drawing Sheets

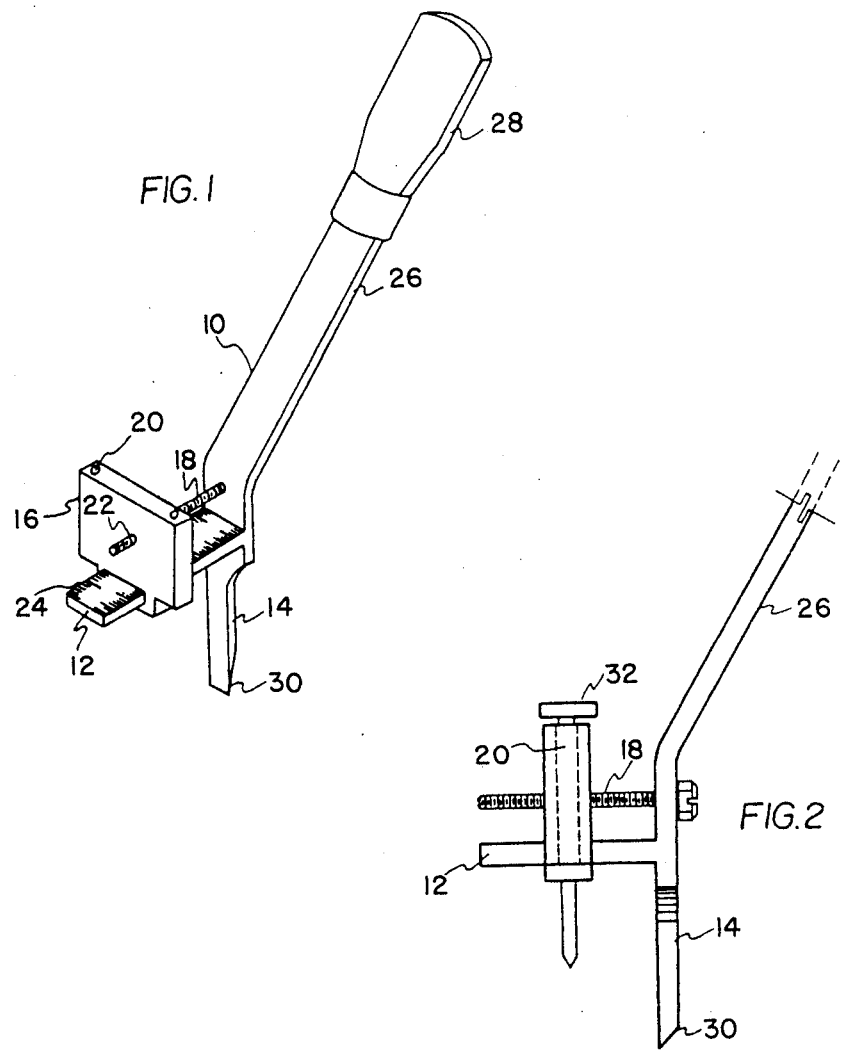
FIG. 1
FIG. 2
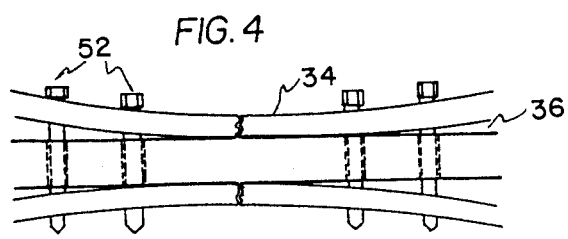
FIG. 4

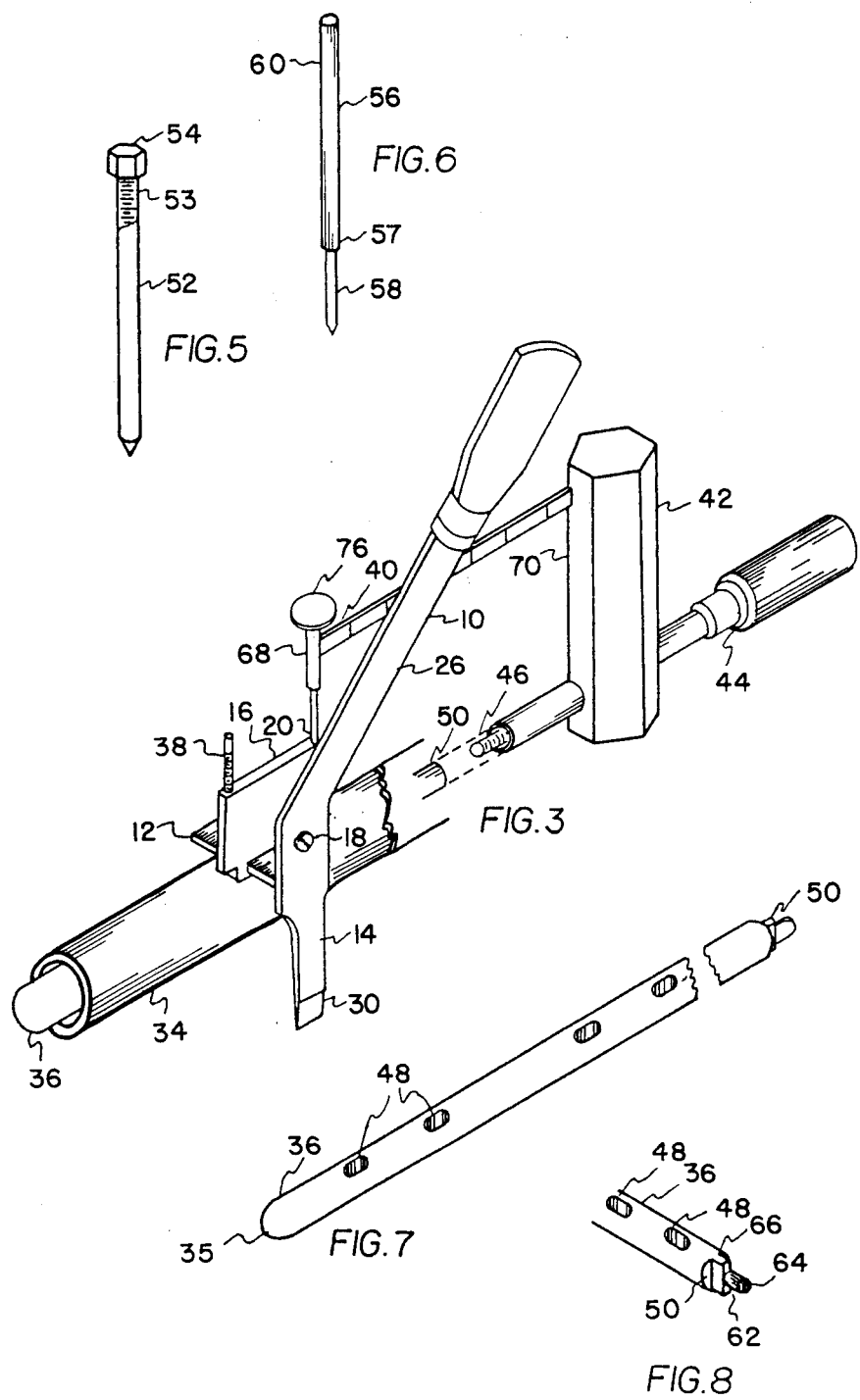

4,978,351

GUIDING INSTRUMENT TO PIERCE THE BONE CORTICAL, AUXILIARY IN THE LOCATION OF THE HOLES FOR INTRA-MARROW PINS

BACKGROUND OF THE INVENTION

Presently fractures and diafissary pseudo-arthroses of femur, tibia and humerus are surgically treated by means of hollow or solid pins provided with a number of orifices or holes located along the longitudinal axis thereof. These are introduced within the marrow channel of the bones, and they are fastened thereto by means of screws or bolts passing freely through the pin orifices, and threaded on the bone cortical, thus forming the bone, pin and bolts into a sole assembly. The formation of a sole assembly assures the stability of the fracture or pseudoarthrosis for the necessary time to provide for the consolidation thereof, and such considerations fundamental to obtain adequate stability of the corresponding bone in order to have the corresponding bone joining.

In addition to fractures and diafissary pseudoarthroses which can be suitably treated with hollow or solid pins, it is also possible to treat osteothomy, tibia or femur shortenings or elongations with these same elements.

The treatment of fractures and the like by means of pins gives the patient the opportunity to carry out his or her normal activities after only a few days following the treatment, and this stimulates the bone joining and, therefore, the expeditous cure of the patient.

The main problem faced by the surgeon when using pins in the treatment of the above mentioned sufferings is to find the pin orifices during the operation, since the implant or pin is already inserted within the bone marrow channel, i. e., out of the sight of the surgeon. In order to solve this problem and to find the pin orifices, nearly all the present day techniques make use of an X-ray apparatus with an image-intensifier, looking that on the screen of this apparatus the images of the pin orifices are superposed to that of a positioner instrument, either of a manual type or constituted as an elongated slider to be affixed to the end of the pin or to the end of an impactor. The bit is introduced through the orifice of the instrument and thus the bone cortical is drilled until the pin orifice is reached. However, there are failures in this technique since it is easy for the bit to slide into the bone surface and, as a consequence thereof, the drilling may not register with the pin orifice.

SUMMARY OF THE INVENTION

Therefore, it is a main object of this invention to design and construct an instrument capable of contributing to the efficient positioning of the intra-marrow pin orifices and which, at the same time, serves as a guide in the drilling of the bone cortical.

It is another object of this invention to construct an instrument auxiliary in the surgical operations in the treatment of fractures and-or diafissary pseudo-arthroses of femur, tibia and humerus, the use of which makes it notoriously easier for the treatment technique and avoids the use of an image intensifier on the X-ray apparatus.

It is further object of this invention to provide an instrument which contributes to the positioning of the orifices of an intra-marrow pin, serving additionally as a guide in the drilling of the bone cortical, which can be used in an opencore or closed-core surgical operation, and assures the perfect location of the intra-marrow pin orifices.

BRIEF EXPLANATION OF DRAWINGS

A detailed description of the instrument forming the subject matter o: this application is offered hereinbelow, making reference to the illustrative drawings, wherein FIG. 1 is a perspective view of an embodiment of the instrument of this invention.

FIG. 2 is an enlarged side view of the instrument of the invention, substantially showing the most important parts thereof.

FIG. 3 is a perspective view showing the use of said instrument during the positioning of the orifices of an intra-marrow pin, and as a guide for the drilling bit.

FIG. 4 shows in a somewhat diagrammatical manner the fixing of an intra-marrow pin in the treatment of a bone fracture.

FIG. 5 shows a screw employed in the fixing of the intra-marrow pin.

FIG. 6 illustrates a pin auxiliary in the fixation of intra-marrow pins to the bone.

FIG. 7 is a partially broken perspective view of an intra-marrow pin.

FIG. 8 is a detailed perspective view of the assembling end of an intra-marrow pin.

DETAILED DESCRIPTION OF THE PREFERRED EMBODIMENTS

Figure 9:
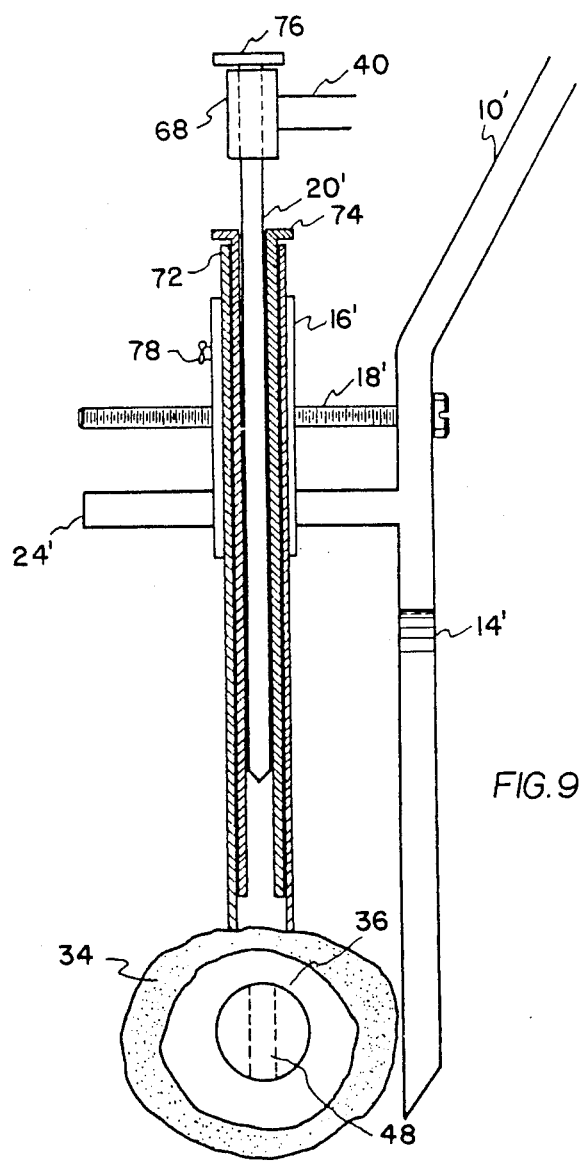
FIG. 9 is a schematic illustration of a second embodiment of the instrument of this invention.

With reference to FIGS. 1 and 2, wherein a first embodiment of the invention is illustrated, it can be seen that the instrument 10 is substantially constituted by an elongated body 26, of width and thickness suitable to resist the surgeon's pushing and assuring the correct application of the instrument on the cortical of the bone being surgically treated. On the upper free end of said body 26, a grip 28 is provided by means of which said instrument 10 can be handled. The opposite end 14 narrows substantially in order to reduce, as much as possible, the incission made by this portion in the patient's tissues. Said portion 14 ends with a sharpened end 30 facilitating likewise the separation of tissue from the bone.

Said instrument 10 is provided with a projection 12 as a part of said elongated body 26, arranged to 90° in respect of the end 14 of said instrument 10. Said projection 12 carries, either on its wider surface or on its longitudinal edge, a gage 24 marked in centimeters and millimeters or else in inches and fractions thereof, on which projection a prismatic or alignment body 16 slides thanks to the screw 18 facilitating the movement toward and from said body 16, relating said body 26 of the instrument, and maintaining the same fastened to the previously selected distance.

The alignment or slidable alignment body 16 has two orifices 20, the use of which will be explained hereinbelow.

As can be clearly seen in FIG. 3 of the annexed drawings, said instrument 10 of this invention is an instrument useful both for finding the orifices of an intra-marrow pin and for guiding a drilling bit. It can be seen in said Figure that the longitudinal position of said orifices 48 on said pin 36 (FIGS. 7 and 8) is assured by the use of an impactor 42, on which both the gaged slide 40 and the end 50 of the intra-marrow pin 36 are mounted. Said gaged slide 40 is provided, at the free end thereof, with a sleeve 68 of suitable diameter, which can be moved to and from the body 70 of said impactor 42, thanks to a butterfly screw (not shown) which is suitably mounted on said body 70 of said impactor 42, and the position thereof according to the calibration thereof, registers exactly the various orifices in said pin 36.

On the other side, said pin 36 is fixed at the end 50 thereof to the threaded end 46 of said impactor 42, with the handle 44 of said impactor 42 rotating suitably, thus establishing the longitudinal distances every orifice 48 has regarding the end 50 thereof.

The alignment body 16 of said instrument 10 must be previously positioned to a suitable distance on said projection 12, according to the thickness of the body cortical being treated, at the corresponding portion thereof, which is determined by means of an X-ray plate previously taken of the patient's member.

In order to effect the affixing of the intra-marrow pin 36 at the bone the surgical treatment of which is being carried out, it is determined, in the first place, into which one of the pin holes is to be inserted the first of said screws 52, whereby the slider 40 is positioned adequately on the body 70 of said impactor 42 and, by means of the piercer 76, a suitably integrated assembly is formed with said impactor 42, said slider 40, said instrument 10 and said pin 36. Likewise, upon knowing from the X-ray plate the thickness of the bone cortical and the radius of pin 36, it is easy to calculate the distance from the bone cortical to which the various holes or orifices 48 of said pin 36 are located and, accordingly, by means of the instrument 10, the drilling of said bone 34 can be carried out with utmost precision, with said bit 38 so as to insert therethrough said screw 52 and threading the same conveniently to the corresponding wall of said bone.

In order to carry out said technique, a pin 36 is positioned at the impactor 42 and introduced into the marrow channel of the bone. The slider 40 is positioned on said impactor 42, so the sleeve 68 registers the more proximal orifice 48 of said pin 36 among those which it is desired to drill. Said instrument 10 is positioned, once previously calibrated, on the cortical of the bone 34, so one of the orifices 20 of said prismatic body 16 is in register with the hole of the sleeve 68 of said slider 40. The piercer 76 is passed through said sleeve 68 of said slider 40, thus connecting both instruments to each other. Through the free end 20 of said intrument 10 a bit 38 of a diameter substantially equal to the diameter of said orifice 20 of said prismatic body 16, is passed through just one cortical of bone 34. Next, a pin 56 is inserted into the hole thus formed. Said piercer 76 and said slider 40 are withdrawn thus clearing the other orifice 20 of said prismatic body 16 and another hole such as that of the Prior orifice is made. A bit with a lesser diameter is inserted through the orifice having no pin 56, so as to enter the orifice 48 of pin 36, and the other cortical is drilled. A screw 52 is positioned into the same orifice, previous to the withdrawal of said instrument 10, and said pin 56 is withdrawn from the other hole, making a drill of a smaller diameter through the other cortical and inserting a second screw 52 (FIG. 5) with a screwdriver with hexahead of suitable dimension, so as to accommodate at the respective cavity thereof the head 54 of said screw 52. Said screws are exclusively threaded onto the first cortical of the bone, by means of the thread 53 and pass freely through said holes 48 of pin 36 and the next cortical.

Thereafter it is proceeded with the positioning, as mentioned above, of the screws on the other side of the fracture, thus completing the affixing of the marrow pin 36 in the bone under surgery.

Finally, the impactor 42 is withdrawn by unscrewing its end 46 by rotating the handle 44, whereby the corresponding surgical operation is practically ended.

In FIG. 5 one of the screws 52 employed in the affixing of the pin 36 has been illustrated, which comprises an elongated body, of circular cross-section, the diameter of which is slightly smaller than the diameter of the holes or orifices 48 of said pin 36, in order that the same are able to slide through said holes from one side to the other of the cortical of said bone, said pin presenting exclusively a threaded zone of screw 52 and a hexagonal head 54, in order to facilitate the threading thereof into the first cortical exposed of the bone being surgically treated. The length of this screw can vary depending on the thickness of the bone being treated.

In FIG. 6 the pin 56 is illustrated presenting a section 58 of smaller diameter and an upper section 60 of greater diameter and substantially greater length, thus establishing a step 57. This pin serves to temporarily maintain the register of the holes drilled into the bone and the holes in the pin 36 and said step 57 has as a purpose serving as a stop against the body of said pin 36, as the diameter of the portion 58 corresponds practically to the diameter of the holes 48 in said pin.

It can be observed in FIGS. 7 and 8 the shape of the pin 36, which can be provided with more than two pairs of holes 48 along the length thereof, there being employed two pairs thereof or all of them, as required by the particular operation being performed. This pin exhibits one pointed end 35 and the opposite end is provided with cutdown portions 50 establishing an intermediate relief 66 from which a sleeve 62 depends with internal threads 64, which serve the purpose of temporarily fastening the impactor 42, as well as the withdrawal of said pin upon the complete healing of the bone.

FIG. 9 represents, in a somewhat schematical form, an embodiment of the instrument 10, wherein like parts are identified with like references, but primed and with a progressive and different numbers those parts having no equivalent in the previously described embodiment.

It is to be observed in this embodiment that the part 14' of said instrument 10' is of a length substantially greater than the corresponding part of said instrument 10, and the prismatic body 16' carries a hole or orifice 20' of diameter substantially greater than that of holes or orifices 20' of Prismatic body 16 in the first embodiment of the invention, in order to accommodate at the interior thereof said sleeve 72 through which the sleeve 74 and the piercer 76 are inserted. Said instrument carries also a butterfly screw 78 or the equivalent thereof to fix to a suitable height said sleeve 72 inside said hole 20'; the height of sleeve 72 depends on the depth of the bone under treatment, as said instrument 10' is useful to make surgical operations under closed-core Practice.

The use of this instrument requires further to the actions provided for said instrument 10, fixing the height of the sleeve 72, as said part 24' of this instrument must rest on the surface of the dermis of the limb under intervention, and the inner end of the bushing of sleeve 72 must be supported firmly on the cortical of said bone 34, as shown in FIG. 9. Obviously, the part 14' of said instrument will be inserted through the tissue of the patient and the surface thereof will be supported also on the cortical of the bone, as depicted.

In order to practice the operation with this instrument, it is required that the sleeve 68 of the slider 40 is joined to one of the orifices 20' of said prismatic body 16' by means of the piercer 76. Through the free orifice 20' of said prismatic body 16' a hole is made on just one cortical, with a bit having the same diameter as the orifice 20', temporarily introducing thereinto a pin 56. Said piercer and slider 40 are withdrawn, and through said sleeve 74 another hole, like the previous one, is made. In this latter hole, with a slender bit passing through the orifice of said pin 36, the other cortical is drilled, positioning thereafter said screw 52 of suitable length with the help of a screw driver, through said sleeve 72, previous to the withdrawal of said sleeve 74. Then the pin 56 is withdrawn and onto said orifice the previous steps are taken. Thereafter the same procedure is carried out on the other side of the fracture.

Although in FIG. 1 of the drawings a specific form has been illustrated for the mounting of the prismatic body 16 on the gaged element 12, it is apparent that some other manner can he employed, without departing from the spirit and scope of the present invention.

It is obvious that the entire instrumental is to be manufactured in stainless steel or any other material suitable to be sterilized, and having a resistance adequate to make pressure therethrough against the walls of the cortical of said bones being subject to surgery.

Regarding the techniques of surgery, although the same do not constitute the subject matter of this invention, it is to be noted that, depending on the fact that the surgery is being effected on a femur, a tibia or an humerus, or if it is of open-core or closed-core type, the same can be slightly varied but, in essence, they follow the above disclosed as regards the use of the instrument object of this invention.

It is to be understood that the above disclosure has been made based on specific embodiments of the invention, and that said instrument can be modified by those skilled in the art, without departing from the spirit of the invention; and it is intended that said changes are considered as a part of this invention, as long as the same are comprised within the scope of the following claims.

What is claimed is:

1. A guiding instrument for drilling a bone cortical, and suitable for use as an auxiliary in positioning or orifices in an intra-marrow pin, comprising:

an elongated flat main body having a first free end provided thereat with a handle for grasping and manipulation thereof, and a second free end narrower than said flat body;

said second free end having a sharpened edge to facilitate and provide for the insertion of said second free end into soft tissue of a patient, and to separate the soft tissue from the bone cortical and free from enveloping the bone;

another flat body transversely oriented to said elongated flat body, positioned between said free ends proximate to said second free end and being provided with a gauge in length units;

an alignment body slidably connected with said other flat body;

a screw connecting said alignment body to said elongated body for controlling and fastening of said alignment body to said elongated flat body;

said alignment body having two holes near narrower edges thereof and running parallel to the faces thereof; and said second end of said elongated body and said other flat body being positioned 90° to each other to provide an effective support of said instrument on the bone cortical.

2. The instrument according to claim 1, wherein said alignment body is provided with holes and includes slide means for sliding said alignment body along said other flat body from and towards said main body to register the prismatic body holes with the holes of the intra-marrow pin for drilling of the bone cortical to implant thereinto screws through the holes of said intra-marrow pin.

3. The instrument according to claim 2, wherein the holes in said alignment body control the guiding of the bit to form the holes in the bone cortical while said instrument is firmly supported on said bone, and said instrument upon withdrawal of the bit permitting the insertion and screwing of the fastening screws for said intra-marrow pin.

4. The instrument according to claim 2, including two concentric sleeves insertable into said holes in said alignment body, said last-mentioned holes having a diameter such that said two concentric sleeves are freely movable therein; the concentric sleeve with the larger diameter having means for fastening thereof to a convenient height relating to said alignment body, and said other concentric sleeve having the narrower diameter serving as a guide for a marking piercer and for the insertion of a drill bit with a substantially equivalent diameter.

5. The instrument according to claim 4, including a butterfly screw for fastening of the outer sleeve to the inner sleeve of said two concentric sleeves on said alignment body.

6. The instrument according to claim 4, wherein the narrower portion of the instrument is greater in length than said sleeves inserted through said alignment body.

7. A method of locating the position to drill a hole into a bone cortical for the insertion of a screw into the bone cortical, comprising:

positioning an intra-marrow pin having spaced orifices therethrough within the bone cortical which is to be pinned;

connecting said intra-marrow pin with an impactor and providing an adjustment mechanism to locate the position of the intra-marrow pin in the bone cortical for insertion of the pins;

positioning an instrument on the outer surface of the skin proximate to the bone cortical to be pinned having the intramarrow pin in the bone cortical;

aligning an alignment body having two orifices forming part of said instrument to use one of said last-mentioned orifices to couple such instrument with said impactor by means of a gauged slide for alignment of said other orifice of said two orifices in said alignment body with one of said orifices and in said intramarrow pin;

pinning said one orifice in said alignment body with said gauged slide for holding the other orifice of said alignment body in registry with said one of two orifices in said other intramarrow bone; and drilling a hole in said bone cortical by inserting a drill into the other orifice of said alignment body for drilling a hole in said bone cortical which is in alignment and registry with said one of said orifices in said intra-marrow pin.

8. The method of claim 7, including using said gauged slide to adjust the positioning of the orifices in said slide in a first direction, providing an adjustment handle for movement of said intra-marrow pin for alignment with said orifices in said alignment body in said first direction, and providing a slide for adjustment of said alignment body in a second direction orthogonal to said first direction for alignment of said other orifice with the said one of said orifices in said intra-marrow pin.

9. An instrument for positioning of intra-marrow pin orifices and to guide a bit for a drilling of a bone cortical, comprising:

an elongated member having a width and thickness suitable to resist a surgeon's pushing and a grip at one end thereof and a substantially narrowed portion at the other end for reducing as much as possible the size of an incision to be made thereby in a patient's tissues, free from enveloping the bone and having a projection positioned between said ends closer to said other end and orthogonal thereto; said projection having a gauge thereon;

a slidable alignment body including sliding means cooperating with said projection for slidably connecting said alignment body with said projection;

screw means coupling said slidable alignment body with said elongated member at a position thereon closer to said other end and locking said slidable alignment body to said elongated member at selected positions on said projection and slidably moving said alignment body by means of said sliding means to different previously selected positions on said projection; and said alignment body being provided with two spaced orifices oriented transversely to said projection for receiving and guiding a bit thereon through one of said last-mentioned two spaced orifices into alignment with an orifice in the intra-marrow pin.

10. The instrument of claim 9, wherein said alignment body has said spaced orifices oriented in a direction following the direction of said narrowed portion and said other end.

11. The instrument of claim 9, wherein said gauge is on a wider surface of said projection.

12. The instrument of claim 9, wherein said gauge is on a longitudinal edge of said projection.

13. The instrument of claim 9, wherein said screw means includes a screw which together with said sliding means facilitates movement of said prismatic body towards and away from said elongated member and maintains said alignment body fastened to said projection.

14. The instrument of claim 9, wherein said other end of said elongated member is provided with a sharpened end to facilitate separation of the patient's tissues from the bone.

15. The instrument of claim 9 for use with an intra-marrow pin having orifices for alignment with orifices provided in said alignment body for guiding the drilling bit into the orifices of said intra-marrow pin; an impactor having a body portion and including a gauged slide coupled with said body portion and an end of said impactor body portion having said intra-marrow pin releasably mounted thereon; and a sleeve connected with said gauged slide for movement towards and away from the body of said impactor for alignment with one of said orifices of said intra-marrow pin.

16. The instrument of claim 15, including a piercer passing through said sleeve and said one of said orifices of said alignment body for adequately positioning said gauged slide on said body of said impactor to form an integrated assembly among said impactor, said gauged slide, said other end of said elongated member and said intra-marrow pin, thereby connecting the impactor with said elongated member and said alignment body, and the other of said orifices of said alignment body is in registry with another of said orifices of said intra-marrow pin to facilitate a drilling operation through the bone to provide an opening therein to connect said other two orifices, one in said intra-marrow pin with the other in said alignment body for positioning therethrough said last-mentioned two orifices and said opening in said bone for placement therein of a pin prior to removal of said instrument.

17. The instrument of claim 9, including:
a movable outer sleeve member insertable into one of the orifices in said alignment body;
means for locking said outer sleeve member to said alignment body to prevent movement relative thereto;
an inner sleeve member insertable into said outer sleeve member; and
a piercer passing through said sleeves, and said sleeve having said piercer passing therethrough being aligned with said inner sleeve member; and said piercer passing through said outer sleeve and said inner sleeve for holding said alignment body and said impactor together.

18. The instrument of claim 15, including:
a movable outer sleeve member insertable into one of the orifices in said alignment body;
means for locking said outer sleeve member to said alignment body to prevent movement relative thereto; an inner sleeve member insertable into said outer sleeve member; and
a piercer passing through said inner sleeve and being aligned therewith; and said piercer also passing through said outer sleeve as well as said inner sleeve for locking said alignment body and said impactor together.

19. The instrument of claim 16, including:
a movable outer sleeve member insertable into one of the orifices in said alignment body, and means for locking said outer sleeve member to said alignment body to prevent movement relative thereto; and
an inner sleeve member insertable into said outer sleeve member, said sleeve having said piercer passing therethrough and being aligned with said inner sleeve member, and said piercer passing through said sleeve and said inner sleeve for locking said alignment body and said impactor together.

* * * * *